(12) United States Patent
Samosky et al.

(10) Patent No.: US 10,060,936 B2
(45) Date of Patent: Aug. 28, 2018

(54) DRUG SIMULANT RECOGNITION SYSTEM AND METHOD OF EMPLOYING

(71) Applicant: UNIVERSITY OF PITTSBURGH—OF THE COMMONWEALTH SYSTEM OF HIGHER EDUCATION, Pittsburgh, PA (US)

(72) Inventors: Joseph T. Samosky, Pittsburgh, PA (US); Douglas A. Nelson, Jr., Meadville, PA (US); Brandon T. Mikulis, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 374 days.

(21) Appl. No.: 14/374,661

(22) PCT Filed: Jan. 25, 2013

(86) PCT No.: PCT/US2013/023140
§ 371 (c)(1),
(2) Date: Jul. 25, 2014

(87) PCT Pub. No.: WO2013/112832
PCT Pub. Date: Aug. 1, 2013

(65) Prior Publication Data
US 2015/0044655 A1   Feb. 12, 2015

Related U.S. Application Data

(60) Provisional application No. 61/591,558, filed on Jan. 27, 2012.

(51) Int. Cl.
*G01N 33/94* (2006.01)
*G01N 33/52* (2006.01)
(Continued)

(52) U.S. Cl.
CPC ............. *G01N 33/94* (2013.01); *G01N 27/00* (2013.01); *G01N 33/52* (2013.01); *G09B 23/28* (2013.01); *G09B 23/285* (2013.01)

(58) Field of Classification Search
CPC ........ G09B 23/28–23/34; G01N 33/52; G01N 33/94; A61M 5/00
(Continued)

(56) References Cited

U.S. PATENT DOCUMENTS

| 5,873,731 A | 2/1999 | Prendergast |
| 6,290,681 B1 | 9/2001 | Brown |

(Continued)

OTHER PUBLICATIONS

Emerson Process Management. "Theory and Application of Conductivity". Rosemount Analytical Inc. Published Jan. 2010. Accessed Sep. 26, 2016. pp. 1-6.*

*Primary Examiner* — Xuan Thai
*Assistant Examiner* — Kristen Shirley
(74) *Attorney, Agent, or Firm* — Eckert Seamans Cherin & Mellott, LLC; Stephen A. Bucchianeri

(57) ABSTRACT

A system for identifying a drug simulant includes an electronic sensing system structured to measure the value of an inherent property of the drug simulant; a processing unit in electrical communication with the electronic sensing system; and a memory unit in communication with the processing unit, the memory unit having a look-up table including a range of values of the inherent property of a given fluid and corresponding names of simulated drugs associated with each value. The processor is structured to identify a name of the simulated drug corresponding to the drug simulant by receiving signals indicative of the value of the measured inherent property from the sensing system and comparing the value to the look-up table in the memory.

14 Claims, 3 Drawing Sheets

(51) Int. Cl.
*G01N 27/00* (2006.01)
*G09B 23/28* (2006.01)

(58) Field of Classification Search
USPC .................................... 434/262–275; 604/19
See application file for complete search history.

(56) References Cited

U.S. PATENT DOCUMENTS

| | | |
|---|---|---|
| 7,927,313 B2 | 4/2011 | Stewart et al. |
| 2011/0009817 A1 | 1/2011 | Bennett et al. |
| 2011/0111794 A1 | 5/2011 | Bochenko et al. |

* cited by examiner

DRUG SIMULANT RECOGNITION SYSTEM AND METHOD OF EMPLOYING

CROSS-REFERENCE TO RELATED APPLICATION

This application claims priority under 35 U.S.C. § 119(e) from U.S. Provisional Application No. 61/591,558, entitled "A Novel Automated Drug Simulant Recognition System for Medical Simulators Based on Direct Fluid Identification", which was filed on Jan. 27, 2012, the disclosure of which is incorporated herein by reference.

FIELD OF THE INVENTION

The present invention relates to systems and methods for use in healthcare training scenarios, and more particularly relates to systems and methods for recognizing drug simulants in healthcare training scenarios.

BACKGROUND OF THE INVENTION

Injection of simulated drugs into a full-body mannequin is frequently performed in simulation-based healthcare training scenarios. Automated drug recognition systems enable objective, real-time sensing and recording of a trainee's performance and, coupled with physiological modeling, can enable the simulator's physical signs to respond automatically and realistically to injected agents.

Current commercial drug recognition strategies based on barcode scanning or RFID tags exhibit some functional limitations. For example, both require an element not present in the actual clinical procedure (such as a barcode or RFID tag attached to the syringe), and both require the labeled or tagged syringe to be brought near a fixed sensor in order for recognition to occur. For example, an RFID antenna built in to the antecubital region of a simulator's arm (front of elbow) will not detect a drug injected into an IV port or manifold located at a distance from the arm, a frequent clinical occurrence. Also, if multiple injections are to be given in rapid sequence, an empty RFID-tagged syringe laid near the arm may interfere with recognition of the next syringe. Additionally, such systems are also not capable of detecting many potential real world errors that may occur. For example, without limitation, such systems are not capable of detecting air embolisms which can result from improper injection technique. Such systems also cannot detect if the total volume of an injected drug has actually entered the body: the failure of the total volume to enter the body may occur, for example, if the drug is injected into a port at a distance from the patient's venous catheter (i.e., via a med line) and the line is not subsequently flushed with saline to ensure that residual drug in the line has been moved into the vein.

As such, there exists a need for improved systems and methods for use in healthcare training scenarios and, more particularly, there exists a need for improved systems and methods for recognizing drug simulants used in healthcare training scenarios.

SUMMARY OF THE INVENTION

In one non-limiting embodiment, the invention provides a system for identifying a drug simulant. The system comprises: an electronic sensing system structured to measure the value of an inherent property of the drug simulant; a processing unit in electrical communication with the electronic sensing system; and a memory unit in communication with the processing unit, the memory unit having a look-up table including a range of values of the inherent property of a given fluid and corresponding names of simulated drugs associated with each value. The processor is structured to identify a name of the simulated drug corresponding to the drug simulant by receiving signals indicative of the value of the measured inherent property from the sensing system and comparing the value to the look-up table in the memory.

The inherent property may comprise one from the group consisting of: conductivity, color, pH and optical refractive index.

In a another non-limiting embodiment, the invention provides an automated drug simulant recognition system for identifying a drug simulant. The system comprises: a port structured to receive a flow of the drug simulant; an electrode chamber in fluid communication with the port and having electrodes disposed therein; a fluid conductivity measuring circuit electrically coupled to the electrodes which outputs a signal corresponding to the conductivity between the electrodes; and a data acquisition interface electrically coupled to the fluid conductivity measuring circuit and structured to receive and digitize the signal and output the signal to a processing device for one or more of analysis, processing and graphical representation.

The system may further comprise a flow meter in fluid communication with the electrode chamber, the flow meter being electrically coupled to the data acquisition interface and structured to communicate output to the data acquisition interface.

The system may further comprise a collection chamber in fluid communication with the flow meter.

The electrodes may be a pair of spaced electrodes formed from stainless steel.

In a further non-limiting embodiment, the invention provides a training system for use in healthcare training. The system comprises: a simulated body having a number of ports disposed thereon, each port being structured to receive a flow of a drug simulant; an automated ding recognition system as previously discussed disposed in the simulated body with the port being disposed at a surface of the simulated body; and a processing device structured to receive and process signals from the data acquisition interface.

The port may comprise at least one of a hand IV port or a antecubitum IV port disposed on the simulated body.

The system may further comprise a flow meter in fluid communication with the electrode chamber, the flow meter being electrically coupled to the data acquisition interface and structured to communicate output to the data acquisition interface.

In a yet further non-limiting embodiment, the invention provides a method for identifying a drug simulant. The method comprises: determining a value of the conductivity of the drug simulant and determining an identity of the drug simulant by comparing the value of the conductivity against a calibration look-up table.

Determining a value of the conductivity of the drug simulant may comprise determining a stable conductivity value by detecting when the derivative of the electrical conductivity signal is less than a predetermined threshold value, then identifying the drug simulant by comparing the stable value of the conductivity against the calibration look-up table.

Determining the identity of the drug simulant by comparing the value of the conductivity against a calibration look-up table may comprise determining the value of the conductivity is within a predetermined range surrounding a calibrated electrical conductivity value for a certain drug in the look-up table.

The method may further comprise continuously measuring the volume of the drug simulant injected even before a stable conductivity value is reached and associating the measured volume with the drug simulant after the identity of the drug simulant is determined.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

DESCRIPTION OF THE PREFERRED EMBODIMENTS

As employed herein, the statement that two or more parts or components are "coupled" together shall mean that the parts are joined or operate together either directly or through one or more intermediate parts or components.

As employed herein, the term "number" shall mean one or an integer greater than one (i.e., a plurality).

As employed herein, the term "simulated body" shall be used to refer to a simulated (i.e., artificial) human or animal body or a portion thereof.

As employed herein, the term "drug simulant" shall mean a fluid intended to serve as a simulated drug which is identifiable as a particular simulated drug by measurement of an inherent property of the fluid.

The present invention provides improved systems and methods for use in healthcare training scenarios for identifying drug simulants. In addressing some of the limitations of available mannequin drug recognition systems, embodiments of the present invention employ a novel sensing system that recognizes an IV-injected agent based on an inherent property of the injected fluid. One example embodiment of the present invention uses varying concentrations of saline to represent different drugs and identification is made via conductivity measurement. The system also determines the rate of injection, the volume administered and the time over which the dose is injected. Simulant solutions in IV bags (e.g., simulated Hextend or crystalloids) can be identified even if the bag is placed at a distance from the body. The system may offer advantages for field training exercises, as no external components (e.g, without limitation, bar codes, RFID tags) need to be attached to the syringe or IV bag.

Figure 1:
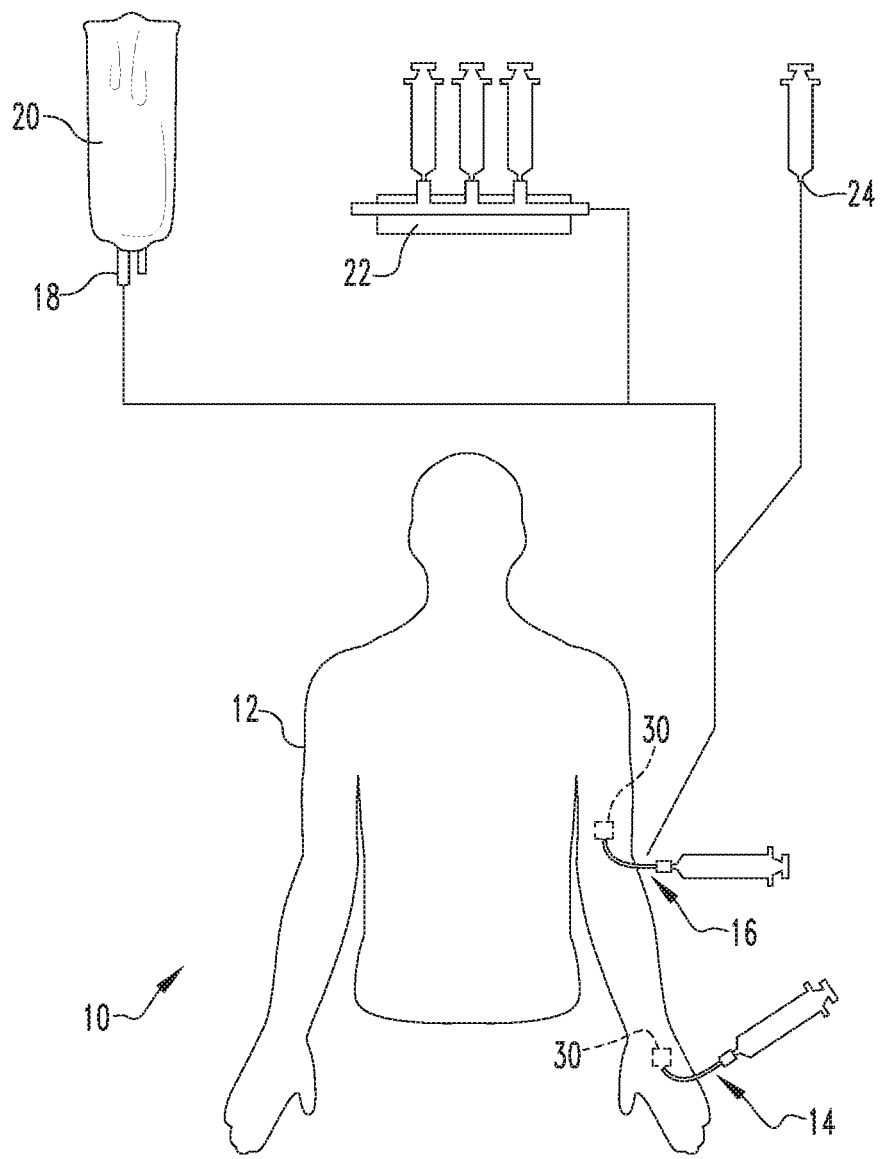
FIG. 1 is a schematic illustration of a training system in accordance with an example embodiment of the present invention.

As illustrated in FIG. 1, a training system 10 in accordance with an example embodiment of the present invention includes a simulated body 12 which is adapted to receive a drug simulant therein through one or more ports as would be found in a real clinical situation. For example, without limitation, such ports on the simulated body 12 may include a back of the hand IV port 14 or an antecubitum IV port 16. Drugs may additionally be injected or otherwise supplied via ports that are disposed a distance from the simulated body 12. Such distant ports may include a port 18 adapted to be coupled to an IV bag 20 hung on an IV pole U bedside (not shown), manifold 22, a remote IV port 24, or via an infusion pump (not shown) that is disposed bedside.

Training system 10 further includes a number of recognition systems 30 disposed inside the simulated body 12 near the IV ports 13 and 16. It is to be appreciated that such placement provides for the most realistic training scenario as such recognition systems are not visible to a student and, as will appreciated from the discussion below, provide for the most immediate results for providing feedback in regard to drug simulant actually received in the simulated body 12. It s also to be appreciated, however, that other placements of recognition system 30 may be employed while still providing an improvement over commercial drug identification strategies such as previously.

As discussed in greater detail below, embodiments of the present invention enable recognition by the training system of drug simulants administered via any of the above described methods, and without any additional elements or procedural steps that are extraneous to the actual clinical procedure, thus enhancing the fidelity of the simulation environment.

Two examples of inherent properties date injected fluid that have been modified and subsequently measured for identification in example embodiments of the present invention in order to encode a drug simulant with a particular drug signature are conductivity and color. When conductivity is the measured property, different drugs are represented by differently conductive solutions. Similarly, through the use of spectrophotometric measurement of the color of a solution, different dyes or combinations of dyes may be added to the solution to encode the identity of a particular drug. A concentration of dye or dyes adequate for spectrophotometric detection may be sufficiently low that when a typical clinically-relevant volume is placed in a vial, syringe or IV line, the solution appears clear and does not exhibit noticeably perceptible color to the human eye. It is to be appreciated that other inherent properties of a solution could be used for identification also, such as pH or optical refractive index. As conductivity can be measured using relatively inexpensive apparatus, and it is simple to formulate salt solutions of varying concentrations which have varying conductivity, the example embodiment described herein utilizes conductivity as the inherent property for identification purposes and varying concentration salt solutions as the drug simulants.

A simple way to vary the conductivity of a solution is to use electrolytes (salts) dissolved in the solution. Design criteria for an example embodiment were that the solution should be optically clear, inexpensive, easy to formulate and safe. In an example embodiment, varying concentrations of saline (sodium chloride) solution were used, however it is to be appreciated that the methodology described herein would work with other electrolytes as well.

Figure 2:
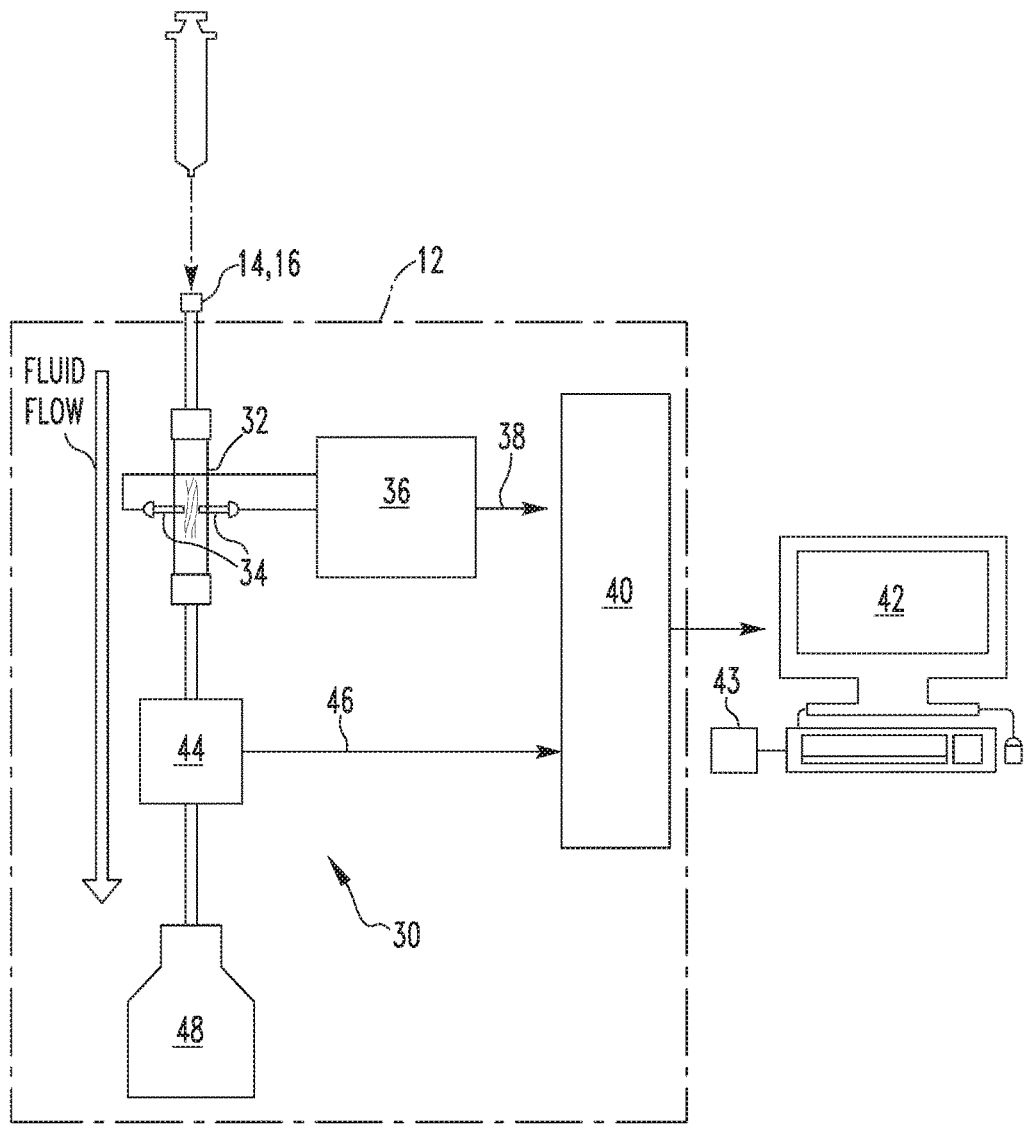
FIG. 2 is a schematic illustration of a drug recognition system in accordance with an example embodiment of the present invention.

FIG. 2 shows a schematic block diagram of an example recognition system 30. A salt solution (not numbered) is provided into any IV line which is coupled to one of the ports (e.g., without limitation, back of the hand IV port 14 or an antecubitum IV port 16) provided on the simulated body 12. Near the surface of the simulated body (preferably inside the simulated body 12) the salt solution enters and flows through a custom-made electrode chamber 32. The chamber 32 includes two electrodes 34 with a gap in between through which the fluid flows. In an example embodiment, stainless steel electrodes were employed, however other materials may be used without varying from the scope of the present invention.

The electrodes 34 are connected to a standard fluid conductivity measuring circuit 36 which applies a low-voltage alternating current (AC) signal to the electrodes 34 and outputs a signal 38 proportional to the conductivity between the electrodes 34. The conductivity signal 38 is digitized by a data acquisition interface 40 and input to a computer 42 or other suitable processing device for analysis, processing and graphical display of the determined results. The computer 42 or other suitable process having access to a memory 43 (either internal or external).

The fluid exiting the electrode chamber then enters a flow meter 44. The output 46 of the flow meter is also digitized by the data acquisition interface 40 and input to the computer 42. The fluid then exits the flow meter 44 and is deposited in a collection chamber 48 which may be disposed internal (such as shown in FIG. 2) or external (not shown) to the simulated body 12. Volume of fluid injected is calculated by integrating the flow rate with respect to time.

As discussed in greater detail below, a drug recognition algorithm embodied in software stored in memory (not numbered) and running on the computer processes and analyzes the information received by the computer to determine the identity and quantity of fluid passing through the system (i.e., fluid that has entered the simulated body 12).

As can be appreciated from the system description provided in conjunction with FIG. 2, in order to recognize the drug simulant, two properties of the fluid are preferably monitored during injection: the flow rate of the injection and the electrical conductivity of the solution being injected. Two novel aspects of the drug recognition algorithm employed are: (a) the identification of when a stable conductivity value occurs during injection and (b) continuous measurement of the volume of drug injected even before a stable conductivity value is reached, with this accumulated value then contributing to the total volume after identification is achieved. These features result in both identification and accurate measurement of the total volume of injected fluid, which may be utilized to provide for a more realistic simulation experience. By continuously monitoring flow rate, the system can identify when an injection begins. When an injection is occurring, the measured flow rate is integrated in time to calculate the volume of injected solution actually received in the simulated body 12. Once a drug is identified, the accumulated volume is then associated with that drug identity. The electrical conductivity, once determined to be stable during injection, is used to identify the injected drug against a calibration look-up table stored in memory contained on the computer 42 or other suitable device.

Figure 3:
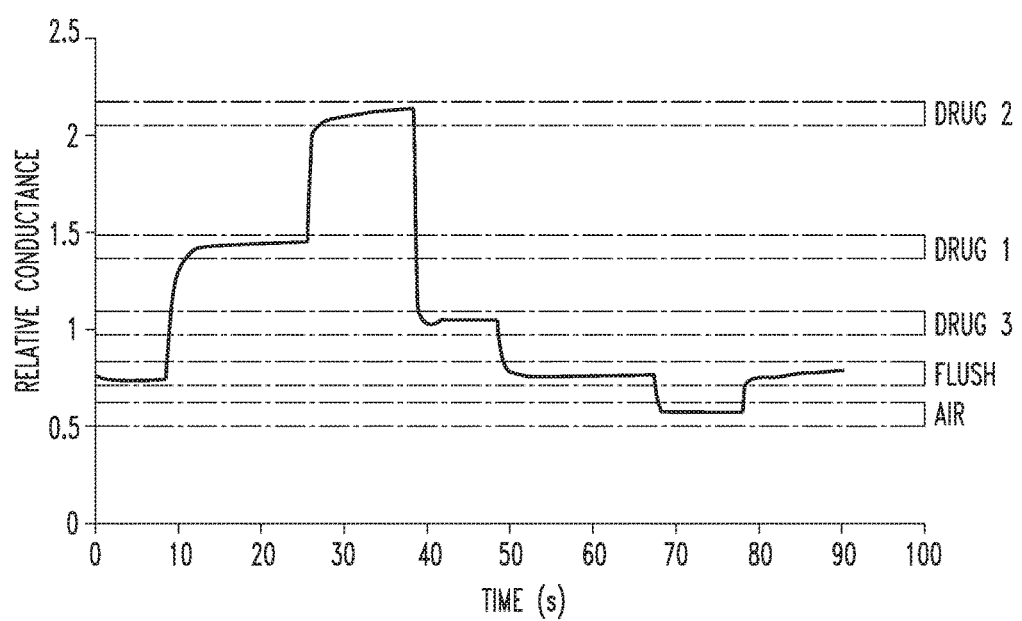
FIG. 3 is a graph showing an example of threshold windows surrounding calibrated electrical conductivity values for an example set of drug simulants in accordance with an embodiment of the invention.

In one implementation to determine when the measured, real-time electrical conductivity during injection has reached a stable value, the derivative $D_N$ of the electrical conductivity signal is first determined. The calculated $D_N$ is compared to threshold values in order to decide if the electrical conductivity of the injected solution is stable or if it is changing. When an injection occurs (i.e. a non-zero flow rate is being measured) the calculated absolute value of $D_N$ is compared to a predetermined rate threshold $R_T$. When $D_N$ becomes less than $R_T$, a stable conductivity value has been reached and the injected drug is identified by comparing its electrical conductivity, $C_N$, with the electrical conductivity values stored in the calibration lookup table ($C_{Drug\_A}$, $C_{Drug\_B}$, $C_{Drug\_C}$, etc). If the injected fluid's electrical conductivity is within a predetermined range (threshold window) surrounding the calibrated electrical conductivity value for a certain drug in the lookup table, the injected fluid is identified as that drug. The threshold windows surrounding calibrated electrical conductivity values are shown in FIG. 3 as dot-dash boxes for each calibrated drug's threshold window.

For example, if $|D_N|<R_T$ during an injection and $C_N$ is within a threshold Window surrounding $C_{Drug\_B}$, the injected fluid is identified as "Drug_B". After this identification occurs, all previously accumulated volume and future accumulated volume during this injection while the absolute value of the derivative $D_N$ remains less than $R_T$, is recorded towards the total volume of the identified drug. Such step is important because if the absolute value of the derivative increases away from zero, this means that a drug with a different electrical conductivity is now being received. If this is the case, volume accumulation for the previously identified drug is ceased (and the total volume recorded) and volume accumulation (starting from 0) for the newly injected drug is commenced. The newly injected drug is then identified once the absolute value of the derivative is once again below the threshold $R_T$ and the newly accumulating volume is then associated with the newly identified drug.

Having thus described the basic functioning of a drug simulant recognition system in accordance with an embodiment of the present invention, three example scenarios in which such drug simulant recognition algorithm can outperform current commercial drug simulant recognition systems in medical simulators will now be discussed.

For the first example, suppose there is a continuous intravenous (IV) infusion: an IV bag containing a drug simulant is hung with its effluent flowing into the simulated patient through a line of tubing at a continuous flow rate. The automated drug recognition system senses the identity and flow rate of the IV fluid, independent of where the bag is hung relative to the patient. Recognition occurs based on the fluid actually entering the simulated patient, not on a device attached to the bag such as an optical bar code or RF ID tag, thus a simulation with more realistic simulated feedback may be provided.

In a second example, now suppose the IV line in the first example is switched to a second, different bag of IV fluid. For example, the second bag may contain a drug that will be infused over a short time, then the line will be switched back to the original IV solution. Independent of whether or not a change in flow rate is discernible due to the switch to the second IV fluid, the algorithm described above will detect the identity and administered volume of the second infused solution, which thus allows for the provision of a more realistic simulation.

For a third example, applicable to anesthesiology training, a multi-port manifold may be placed near a simulated patient's head, permitting various drugs to be administered to the simulated patient by a physician positioned near the patient's head. This arrangement is common during an operation. Multiple syringes may be connected to the manifold for making rapid, remote injections into the patient. The length of tubing between the manifold and the catheter placed in the patient's vein introduces "dead space" for fluid. Fluid in this dead space has not yet entered into the patient and is not benefitting the patient. A common practice when using this injection arrangement is to follow a drug injection into the manifold with a saline flush, an injection of saline in which the injected volume of saline is at least as large as the volume of dead space in the tubing. This ensures that the full volume of a drug injected into the line is pushed into the patient's vein. The system is initially primed with saline solution in order to not introduce air into the patient during injection.

As an example simulation scenario, let us assume that there are 4 milliliters of dead space in the tubing, and that a trainee is to inject 10 milliliters of "Drug A" into the line, followed by a 10 milliliter saline flush to clear Drug A from the line's dead space, pushing Drug A fully into the simulated patient. If the sequence of two injections is properly performed, the automated drug recognition system described herein would recognize, first, 4 ml of saline entering the patient (the saline initially present in the line), followed by 10 ml of Drug A, then 6 ml of saline flush. 4 ml of the 10 ml saline flush would remain in the tubing at the end of the sequence of two injections.

If the trainee made the error of not performing the 10 ml saline flush, then the automated drug recognition system would sense, first, 4 ml of saline entering the patient, followed by only 6 ml of Drug A, with 4 ml of Drug A remaining in the dead space of the tubing, not entering the simulated patient. The system could then alert the trainee that this error had occurred, and provide immediate feedback that flushing the line with saline is necessary to ensure the entire volume of an administered drug actually enters the simulated body.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A system for identifying drug simulants that serve as surrogates for real drugs, the system comprising:
   a plurality of drug simulants in liquid form, each of the drug simulants having a common inherent property which has been selectively modified among the plurality of simulants in a predetermined manner such that each drug simulant may be uniquely identified from the other drug simulants by measurement of the value of said inherent property;
   a port structured to receive a flow of a drug simulant from among the plurality of drug simulants;
   an electronic sensing system in communication with the port, the electronic sensing system being structured to measure the value of the inherent property of the drug simulant received by the port;
   a processing unit in electrical communication with the electronic sensing system; and
   a memory unit in communication with the processing unit, the memory unit having a look-up table including a plurality of predetermined ranges of values of the inherent property of the drug simulants, each range being associated in a predetermined way with a corresponding name of a real drug,
   wherein the processing unit is structured to identify the name of the real drug corresponding to the drug simulant received by the port by receiving signals from the sensing system indicative of the value of the measured inherent property of the drug simulant and comparing the value to the predetermined ranges of values in the look-up table in the memory unit.

2. The system of claim 1 wherein the inherent property comprises one from the group consisting of: conductivity, color, pH and optical refractive index.

3. The system of claim 1 further comprising:
   an electrode chamber in liquid communication with the port,
   wherein the electronic sensing system comprises:
      a plurality of electrodes disposed in the electrode chamber;
      a liquid conductivity measuring circuit electrically coupled to the electrodes which is structured to output a signal corresponding to the conductivity between the electrodes; and
      a data acquisition interface electrically coupled to the liquid conductivity measuring circuit and which is structured to receive and digitize the signal corresponding to the conductivity between the electrodes and output the signal to the processing unit.

4. The system of claim 3 further comprising a flow meter in liquid communication with the electrode chamber, the flow meter being electrically coupled to the data acquisition interface and structured to communicate output to the data acquisition interface.

5. The system of claim 4 further comprising a collection chamber in liquid communication with the flow meter.

6. The system of claim 3 wherein the electrodes are a pair of spaced electrodes formed from stainless steel.

7. The system of claim 3 further comprising a portion of a simulated human body, wherein the port is disposed on the portion of the simulated human body.

8. The system of claim 7 wherein the port comprises at least one of a hand IV port or an antecubitum IV port disposed on the simulated human body.

9. The system of claim 1 wherein the system further comprises a portion of a simulated human body, and wherein the electronic sensing system is disposed in the portion of the simulated human body.

10. The system of claim 1 wherein the system further comprises a portion of a simulated human body, and wherein the electronic sensing system is disposed on the portion of the simulated human body.

11. The system of claim 1 wherein the measured inherent property is conductivity.

12. The system of claim 11 wherein the processing unit is further programmed to:
   determine a stable conductivity value by detecting when the derivative of the number of signals indicative of the value of the measured inherent property of the liquid is less than a predetermined threshold value, and
   identify the name of the real drug by comparing the stable conductivity value against the look-up table in the memory unit.

13. The system of claim 12 wherein the processing unit is programmed to identify the name of the real drug by comparing the stable conductivity value against the look-up table in the memory unit by determining that the value of the conductivity is within a predetermined range surrounding a calibrated electrical conductivity value for a certain real drug in the look-up table in the memory unit.

14. The system of claim 12 wherein the processing unit is further programmed to continuously measure a volume of the liquid injected even before a stable conductivity value is reached and associate the volume measured with the liquid after the name of the real drug corresponding to the liquid is determined.

* * * * *

UNITED STATES PATENT AND TRADEMARK OFFICE
CERTIFICATE OF CORRECTION

Page 1 of 1

PATENT NO. : 10,060,936 B2
APPLICATION NO. : 14/374661
DATED : August 28, 2018
INVENTOR(S) : Joseph T. Samosky et al.

It is certified that error appears in the above-identified patent and that said Letters Patent is hereby corrected as shown below:

In the Specification

Column 2, Line 39, "ding" should read --drug--.
Column 4, Line 6, "U" should read --at--.
Column 4, Line 17, "s" should read --is--.
Column 4, Line 28, "date" should read --of the--.
Column 6, Line 9, "Window" should read --window--.

Signed and Sealed this
Sixth Day of November, 2018

Andrei Iancu
*Director of the United States Patent and Trademark Office*